US010329560B2

(12) United States Patent
Williams et al.

(10) Patent No.: US 10,329,560 B2
(45) Date of Patent: *Jun. 25, 2019

(54) TARGETING NON-CODING RNA FOR RNA INTERFERENCE

(71) Applicant: Georgia Tech Research Corporation, Atlanta, GA (US)

(72) Inventors: Loren D. Williams, Atlanta, GA (US); Po-Yu Fang, Atlanta, GA (US); Chiaolong Hsiao, Atlanta, GA (US); Justin Williams, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/911,618

(22) PCT Filed: Sep. 23, 2014

(86) PCT No.: PCT/US2014/056904
§ 371 (c)(1),
(2) Date: Feb. 11, 2016

(87) PCT Pub. No.: WO2015/042556
PCT Pub. Date: Mar. 26, 2015

(65) Prior Publication Data
US 2016/0194632 A1  Jul. 7, 2016

Related U.S. Application Data

(60) Provisional application No. 61/881,068, filed on Sep. 23, 2013.

(51) Int. Cl.
*C12N 15/11* (2006.01)
*C12N 15/113* (2010.01)
*A01N 25/00* (2006.01)
*A01N 25/34* (2006.01)
*A01N 57/16* (2006.01)
*C12N 15/88* (2006.01)

(52) U.S. Cl.
CPC .......... *C12N 15/113* (2013.01); *A01N 25/006* (2013.01); *A01N 25/34* (2013.01); *A01N 57/16* (2013.01); *C12N 15/111* (2013.01); *C12N 15/88* (2013.01); *C12N 2310/14* (2013.01); *C12N 2320/32* (2013.01); *C12N 2330/50* (2013.01); *C12N 2795/18123* (2013.01); *C12N 2795/18142* (2013.01)

(58) Field of Classification Search
None
See application file for complete search history.

(56) References Cited

U.S. PATENT DOCUMENTS

| 8,252,535 | B2 | 8/2012 | Biekle |
| 8,324,366 | B2 | 12/2012 | Akinc |
| 8,329,888 | B2 | 12/2012 | Wengel |
| 2006/0021087 | A1 | 1/2006 | Baum |
| 2006/0200878 | A1 | 9/2006 | Lutfiyya |
| 2010/0184209 | A1 | 7/2010 | Vermeulen |
| 2011/0213006 | A1 | 9/2011 | Hasan |
| 2011/0301223 | A1 | 12/2011 | Broglie |
| 2011/0319475 | A1 * | 12/2011 | Collard ............ A61K 31/7088 514/44 A |
| 2012/0252718 | A1 | 10/2012 | Yang |
| 2012/0297501 | A1 | 11/2012 | Beghyn |
| 2013/0125260 | A1 | 5/2013 | Bailey |

FOREIGN PATENT DOCUMENTS

| AU | 2011253615 | 12/2011 | |
| WO | 9107182 | 5/1991 | |
| WO | 03106657 | 2/2003 | |
| WO | 2005068629 | 7/2005 | |
| WO | 2006130976 | 12/2006 | |
| WO | 2008156702 | 12/2008 | |
| WO | WO-2011044238 A1 * | 4/2011 | ............ C12N 15/11 |
| WO | 2012055982 | 5/2012 | |
| WO | 2013075233 | 5/2013 | |
| WO | 2013117910 | 8/2013 | |

OTHER PUBLICATIONS

Srisawat et al, Sephadex-binding RNA ligands: rapid affinity purification of RNA from complex RNA mixtures, 2001, Nucleic Acid Research, vol. 29, 2: 1-5.*
Wei et al, Development of an antisense RNA delivery system using conjugates of the MS2 bacteriophage capsids and HIV-1 TAT cell penetrating peptide, 2009, Biomedicine & Pharmacotherapy, 63: 313-318.*
Bowman, et al., Preparation of long templates for RNA in vitro transcription by recursive PCR , Methods Mol Biol., 941:19-41 (2012).
Galaway and Stockley, MS2 viruslike particles: a robust, semisynthetic targeted drug delivery platform , Mol Pharm., 10(1):59-68 (2013).
Haussrcker, The business of rnai therapeutics in 2012 , Mol Ther Nucleic Acids , 1:e8. doi: 10.1038/mtna.2011.9. (2012).

(Continued)

*Primary Examiner* — Ekaterina Poliakova-Georgantas
(74) *Attorney, Agent, or Firm* — Smith, Gambrell & Russell, LLP; Charles Vorndran

(57) ABSTRACT

A broad and extensive new category of targets for ribonucleic acids (RNAs) with interference activity (iRNAs), exclusive of the traditional messenger RNA (mRNA) targets have been discovered. iRNAs can be used to manipulate biological processes that do not explicitly involve mRNA and can be directed at non-coding RNAs, such as ribosomal RNAs (rRNAs) and transfer RNAs (tRNAs). iRNA sequences targeted at ribosomal rRNAs and tRNAs have been designed and tested. iRNA that targets a non-coding RNA is called non-coding interfering RNA (nciRNA). nciRNAs cause degradation of non-coding RNAs in vivo, and are highly active in biological assays. nciRNAs can be used as programmed toxins for specific targeting of eukaryotic pathogens and for protection of plants and structures from insects and weeds.

5 Claims, 4 Drawing Sheets

Specification includes a Sequence Listing.

(56) References Cited

OTHER PUBLICATIONS

Huang, et al., Efficient and specific gene knockdown by small interfering RNASs produced in bacteria, Nature Biotch., 31(4):350-6 (2013).
Huvenne and Smagghe, Mechanisms of dsrna uptake in insects and potential of rnai for pest control: A review, J Insect Physiol., 56:227-35 (2010).
Li and Chen, Targeting long-noncodingRNAs in cancer: Progress and prospects, Intl J Biochem Cell Biol., 45(8):1895-910 (2013).
Mallik, et al., RNAi for the large non-coding hsr [omrga] transcripts suppresses polyglutamine pathogenesis in *Drosophila* models, RNA Biol., 6(4):464-76 (2009).
Milhavet, et al., RNA interference in biology and medicine, Pharmacol Rev., 55: 629-648 (2003).
Nicolas, et al., Loss and retention of RNA interference in fungi and parasites, PLoS, 9(1):e1003089 (2013).
Oey, et al., Rnai knock-down of lhcbm1, 2 and 3 increases photosynthetic h2 production efficiency of the green alga *Chiamydomonas reinhardtii*, PLoS One, 8:e61375 (2013).
Pan, et al., Development of a microrna delivery system based on bacteriophage ms2 virus-like particles, FEBS J, 279:1198-1208 (2012).
Wilson, The A-Z of bacterial translation inhibitors, Crit Rev Biochem Mol Biol., 44(6):393-433 (2009).

Xiang, et al., Short hairpin RNA-expressing bacteria elicit RNA interference in mammals, Nature Biochem., 24(6):697-702 (2006).
Yu, et al., Altered long noncoding RNAS expressions in dorsal root ganglion after rat sciatic nerve injury, Neurosci Lttrs., 534(26):117-22 (2013).
Zheng, et al., RNAi-mediatrd targeting of noncoding and coding sequences in DNA repair gene messages efficiently radiosensitizes human tumor cells, Cancer Res., 72(5):1221-8 (2012).
Zhou, et al., RNA interference in the termite *Reticulitermes flavipes* through ingestion of double-stranded RNA, Insect Biochem Mol Biol., 38: 805-15 (2008).
International Search Report for corresponding PCT application PCT/US2014/055904 dated Jan. 23, 2015.
Bielke, Wolfgang, et al., "Composition for Inhibiting Expression of One or More Target Genes in a Eukaryotic Cell Comprises One or More Genetic Constructs Comprising a Target Gene and a Small Interfering RNA Tag", English Abstract of Bibliographic Data: DE102006016365(A1), Oct. 11, 2007.
Lüke, Wolfgang, et al., "Down Regulation of the Gene Expression by Means of Nucleic Acid-Loaded Virus-Like Particles", English Abstract of Bibliographic Data: WO 2009/036933, Mar. 26, 2009.
Xu, Song et al., "Long Non-Coding RNA Sequence Relevant to Human Melanoma Cells and Application Thereof", English Abstract of Bibliographic Data: CN101633923(A), Jan. 27, 2010.
Zhong, Kang, et al., "Method, Special Plasmid and Function Nucleotide Segment for Obtaining Male Sterile Wheat", English Abstract of Bibliographic Data: CN1548539(A), Nov. 24, 2004.

\* cited by examiner

TARGETING NON-CODING RNA FOR RNA INTERFERENCE

This application is a 371 application of International Application No. PCT/2014/056904, filed Sep. 23, 2014, which claims priority to and benefit of U.S. Provisional Patent Application No. 61/881,068 filed on Sep. 23, 2013.

STATEMENT REGARDING FEDERALLY SPONSORED RESEARCH OR DEVELOPMENT

This invention was made with Government Support under Agreement NAI awarded to Loren D. Williams by the NASA Astrobiology Institute, Contract number NNA09DA78A. The Government has certain rights in the invention

REFERENCE TO SEQUENCE LISTING

The Sequence Listing submitted on Feb. 11, 2016 as a text file named "GTRC$_{13}$6432$_{13}$ ST25.txt," created on Sep. 23, 2014, and having a size of 3,384 bytes is hereby incorporated by reference pursuant to 37 C.F.R. § 1.52(e)(5).

FIELD OF THE INVENTION

The invention relates to the field of controlling gene expression in particular to the application of RNA interference.

BACKGROUND OF THE INVENTION

Ribonucleic acid (RNA) is a biological polymer that plays key roles in transcription, translation and many other biological functions. Over the last several decades RNA has been found to play a variety of regulatory roles in gene expression. In a phenomenon known as RNA Interference (RNAi), a RNA molecule of appropriate sequence will down-regulate expression of a given gene by preventing the corresponding messenger RNA (mRNA) from producing protein. RNA with interference activity is known as an iRNA and has the capability to cause degradation of an mRNA. When an iRNA forms complementary Watson-Crick base pairs with an mRNA, it induces mRNA cleavage by accessory proteins. The source of the iRNA can be viral infection, transcription, or introduction from exogenous sources.

RNAi has been rapidly developed into a potent and broadly applied tool, with applications in medicine, biofuels, agriculture and basic research. RNAi therapeutics center on down-regulating the expression of genes that are over-expressed in disease states. Up-to-date information of medical applications of RNAi is available. Beyond medicine, RNAi is widely used to manipulate and evaluate gene expression in eukaryotic systems. Alternative mechanisms for RNAi-based technologies have significant potential.

It is an object of the current invention to provide compositions and methods for the RNA interference of non-coding RNAs.

SUMMARY OF THE INVENTION

A broad and extensive new category of targets for RNAs with interference activity (iRNAs), exclusive of the traditional messenger RNA (mRNA) targets have been discovered. iRNAs can be used to manipulate biological processes that do not explicitly involve mRNA and can be directed at non-coding RNAs, such as ribosomal RNAs (rRNAs) and transfer RNAs (tRNAs).

iRNA sequences targeted at ribosomal rRNAs and tRNAs have been designed and tested. iRNA that targets a non-coding RNA is called non-coding interfering RNA (nciRNA). nciRNAs cause degradation of non-coding RNAs in vivo, and are highly active in biological assays. nciRNAs can be used as programmed toxins for specific targeting of eukaryotic pathogens and for protection of plants and structures from insects and weeds.

Ribonucleic acid, which is a polyribonucleotide, is capable of causing interference activity against a non-coding RNA target (ncRNA) include a nucleotide sequence complementary to a target RNA within a target organism, where the target RNA is a non-coding RNA (ncRNA) and where binding of the nciRNA to the target RNA causes degradation of the target RNA. Typically the target organism is a eukaryote and the nciRNA or nciRNA precursor is expressed in a prokaryote. nciRNAs can be of any size and can be of any sequence that is complementary to a non-coding RNA target. In some embodiments the nciRNA is produced within the target organism by in vivo processing of a precursor of the nciRNA.

Typically the nciRNA targets the translational machinery of a eukaryote, such as ribosomal RNA (rRNA) or transfer RNA (tRNA). In one embodiment the target of the nciRNA is the large subunit ribosomal RNA (28S rRNA).

Virus-like particles (VLPs) containing ribonucleic acids capable of causing interference activity against eukaryotic non-coding RNA targets are also disclosed. VLPs containing nciRNAs include a virus-like particle formed from the coat proteins of a bacteriophage and one or more nciRNAs encapsulated within the viral particle. The one or more nciRNAs are fused to a nucleotide sequence with high affinity for the bacteriophage or virus coat protein. In some embodiments the RNA packaged within the VLP is a double-stranded RNA (dsRNA) precursor that is processed to a biologically active nciRNA within the target cells. In one embodiment the nciRNAs encapsulated within VLP optionally include a sequence that facilitates purification of the RNA.

Methods for the in vivo expression and packaging of nciRNA and/or precursor polynucleotides within VLPs are also provided. The methods include engineering a recombinant bacteria cell to express one or more genes encoding the coat protein of a bacteriophage and genes encoding an RNA that is a nciRNA or dsRNA precursor. The RNA contains a nucleotide sequence with high affinity for the bacteriophage coat protein, to enable uptake of the RNA within the VLP. The methods also include expressing the RNA and coat protein constructs in the cell and purifying the VLPs containing nciRNAs or nciRNA precursors.

Bacterial cells engineered to express nciRNAs, nciRNA precursors of nciRNAs and/or VLPs containing nciRNAs are also disclosed.

DETAILED DESCRIPTION OF THE INVENTION

I. Definitions

Figure 1:
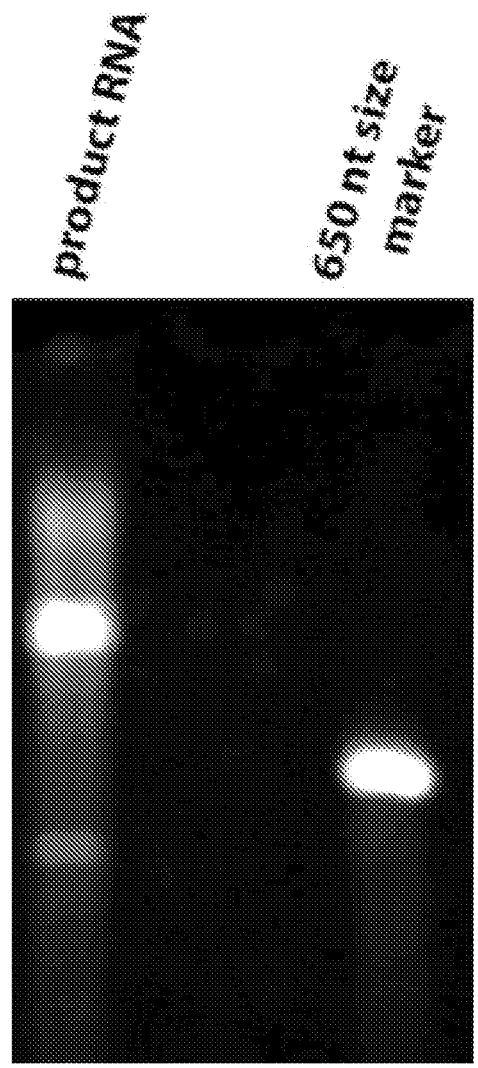
FIG. 1 is an image of a denaturing polyacrylamide gel of RNA which was packaged into a VLP by co-expression of the capsid protein and the RNA in vivo. The most intense band in the lane labeled "product RNA" corresponds to the encapsulated RNA including the duo tags, which is 751 nucleotides in length. mRNA encoding the capsid protein is shown as the faint band in the left lane below the position of the 650 nt size marker band. The single band corresponding to the 650 nucleotide size marker is the shown in the lane on the right.
Figure 2:
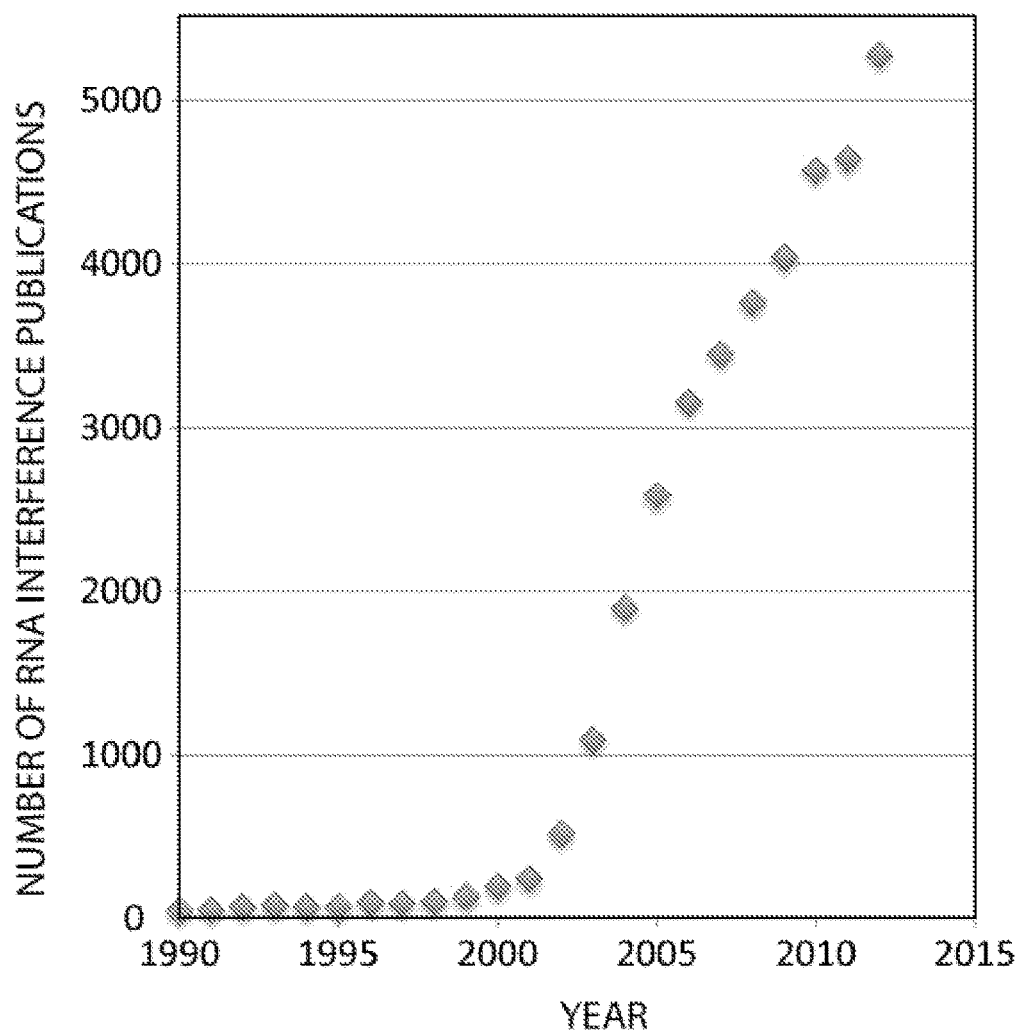
FIG. 2 is a scatter dot plot showing the number of RNA interference publications over a period of time (years). The data displayed was acquired from the NCBI Pubmed database, using the search term "RNA Interference".

The term "host cell" refers to prokaryotic and eukaryotic cells into which a recombinant expression vector can be introduced.

The terms "transformed" and "transfected" encompass the introduction of a nucleic acid (e.g., a vector) into a cell by a number of techniques known in the art.

The term "specifically binds" to a target refers to a binding reaction which is determinative of the presence of the molecule in the presence of a heterogeneous population of other biologics.

"Localization Signal" or "Localization Sequence" or "Recognition Sequence" or "Targeting Signal" or "Targeting Sequence" or "Recognition Tag" or "Recognition polynucleotide" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location.

The term "vector" refers to a replicon, such as a plasmid, phage genome, or cosmid, into which another DNA segment may be inserted so as to bring about the replication of the inserted segment or the expression of the inserted segment as RNA or protein. The vectors described herein can be expression vectors.

The term "expression vector" refers to a vector that includes one or more expression control sequences.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "iRNA" refers to a ribonucleic acid (RNA) molecule which can bind by complementary base pairing to target messenger RNA transcripts (mRNAs), or to non-coding RNAs, usually causing translational repression or target degradation which results in gene silencing or other downstream effects such as translational suppression by degradation of ribosomal RNA. Exemplary iRNA molecules include but are not limited to siRNA and microRNA.

The terms "target gene" and "target sequence" are used interchangeably and refer to a sequence that can hybridize with an iRNA and induce gene silencing and other downstream effects.

The terms "individual," "individual," "subject," and "patient" are used interchangeably herein, and refer to a mammal, including, but not limited to, humans, rodents, such as mice and rats, and other laboratory animals.

The terms "virus like particle", or "VLP" refer to a viral or phage capsid formed from the assembly of viral or phage coat proteins, that does not contain viral genetic material. A "VLP-RNA" is a recombinant virus like particle containing a capsid of viral or bacteriophage coat proteins that can contain one or more RNA molecules enclosed within the capsid.

II. Compositions for Non-Coding RNA Interference

A broad and extensive category of targets (non-coding RNA) for interfering RNAs has been discovered. RNA with interference activity can be used to manipulate biological processes that do not explicitly involve messenger RNA and can be directed at non-coding RNAs, such as ribosomal RNA and transfer RNA. RNAs with interfering activity against non-coding targets (nciRNAs) are disclosed. Compositions for the efficient expression and delivery of nciRNAs are also provided. In some embodiments, nciRNAs are enclosed within virus like particles (VLPs).

A. RNA Interference of Non-Coding Targets

A traditional iRNA (an RNA molecule with interference activity) of appropriate sequence will prevent or reduce protein expression from a specific gene by causing degradation of mRNA. When an iRNA molecule forms complementary Watson-Crick base pairs with an mRNA, it induces mRNA cleavage by accessory proteins. The source of the iRNA can be viral infection, transcription, or introduction from exogenous sources.

iRNA sequences targeted at non-coding RNAs, such as ribosomal RNAs (rRNAs) and transfer RNAs (tRNAs), have been designed and tested. iRNA that targets a non-coding RNA is referred to as RNA with interfering activity against non-coding targets (nciRNA). nciRNAs cause degradation of non-coding RNAs in vivo, and are highly active in biological assays. nciRNAs can be used as programmed toxins for specific targeting of eukaryotic pathogens and for protection of plants and structures from insects and weeds. Furthermore, in vivo synthesis of nciRNA and nciRNA precursors in prokaryotic expression systems such as *Escherichia coli* is adaptable and reliable.

1. Targets of nciRNA

An nciRNA polynucleotide is highly specific for a non-coding target RNA within a target organism or group of organisms. Typically the target organism is a eukaryotic organism, such as a plant, animal, alga or fungus. Typically the target gene is not a naturally occurring viral gene.

nciRNAs can be specifically designed to have interference activity against a target non-coding RNA. Non-coding RNAs include ribosomal RNA (rRNA), transfer RNA (tRNA), small nucleolar RNA (snoRNA), small nuclear RNA (snRNA or URNA) and extracellular RNA (exRNAs). In some embodiments the target for nciRNA is the translational machinery of eukaryotic cells, such as the rRNAs of either the small or large ribosomal subunit. In some embodiments an nciRNA is designed to target two or more non-coding RNAs. In other embodiments the nciRNA is designed to target a single non-coding RNA. The one or more target non-coding RNAs can be of any desired sequence and may be of any size. In one embodiment the nciRNA is the large subunit ribosomal RNA (28S rRNA).

An exemplary nciRNA sequence targeting the large subunit ribosomal RNA (28S rRNA) is 5'

(SEQ ID NO. 1)
rGUCCGAGUAAUUUACGUUUUGAUACGGUUGCGGAACUUGCGGGGUGCC

UAUUGAAGCAUGAGCCGGCGACUCAGCCGUAAGGCUGGACCCGAAACC

GGGCGAGCUAGCCCUGGCCAGCCGUAAGGCGAACCGGUGGGGAUGCA

AACCCCUCGGAUGAGCUGGGGCUAGGAGUGAAAAGCUAACCGAGCCCG

GAGAUAGCUGGUUCUGCCGUAAGGCAGCGUUGCCGUAAGGCAAGUGCG

AAUGCCGGCAUGAGUAACGAGCGGGAGAACCCUCGCCAAGGAACUCUG

CAAGCCGUAAGGCCUCUGGCGACUGUUUACCAAAAACACAGCGCCGUAA

GGCGCGAGCCGUAAGGCUAACGACCGGAGCGCUGUCUCGGCGAGGGACC

CGGUGAAAUUGAACUGGCCGUGAAGAUGCGGCCUACCCGUGGCAGGAC

GAAAAGACCCCGUGGAGCUUUACUGCCGUAAGGCAGUUUGACUGGGGC

GGUCGGCCGUAAGGCUAAAAGUUACCCCGGGGAUAACAGGCUGAUCGC

CGUAAGGCGGUUUGGCACCUCGAUGUCGGCUCGUCGCGCCGUAAGGCU

UGGGCUGUUCGCCCAUUAAAGCGGCACGCGAGCUGGGUUCAGAACGUC

GUGAGACAGUUCGGUCUCUAUCCGCCACGGGCUUCCUCGUGCUUAGUA

ACUAAGGAUGAAAUGCAUGUCUAAGACAGCAUCUUCGC 3'.

2. Target Organisms nciRNAs can be designed for essentially any desired degree of species specificity. In some embodiments nciRNAs are directed at one organism or group of organisms, such as a single species. In other embodiments nciRNAs are designed to have RNA interference activity in a broad range of target organisms or species. The target RNA can be universally conserved amongst eukaryotes, or can be conserved amongst a group of organisms. Exemplary groups include eukaryotes within a kingdom, such as the kingdom Animalia, the kingdom Plantae or the kingdom Protista. In other embodiments the target RNA is universally conserved amongst eukaryotes in a given phylum. Exemplary phyla include Arthropoda, Brachiopoda, Chorrdata, Mollusca, Nematoda and Annelida. In other embodiments the target RNA is universally conserved amongst all eukaryotes within a phylogenetic class or order. In some embodiments the target RNA is universally conserved amongst all eukaryotes within a genus, or within a species. For example, it is possible to target the rRNA of Isoptera (termites) and Hymenoptera (bees, wasps and ants) or to target the rRNA of Isoptera and not Hymenoptera.

3. Structure of nciRNAs

Typically nciRNAs are polynucleotides of 21-23 nucleotides in length. The nucleotide sequence of an nciRNA polynucleotide is complementary to the sequence of the non-coding target RNA. In some embodiments the sequence of the nciRNA is 100% complementary to the sequence of the target RNA. In other embodiments the nciRNA is less than 100% complementary to the target RNA. The sequence of the nciRNA can be at least 95%, at least 90%, at least 85%, at least 80%, at least 75%, or at least 70% complementary to the nucleotide sequence of the target gene, so that sequence variations that can occur, for example due to genetic mutation, evolutionary divergence and strain polymorphism can be tolerated.

4. dsRNA Precursors of nciRNAs

In some embodiments, nciRNAs are produced in the target organism from RNA precursors. In some embodiments a nciRNA precursor is a double stranded RNA (dsRNA) that is at least 24 nucleotides in length. Precursor dsRNA is processed into a biologically active nciRNA by the activity of the endogenous cellular enzymes within the target organism. Exemplary enzymes that process precursor RNAs into nciRNAs include the enzyme Dicer, as well as other Dicer-like enzymes and accessory proteins such as the RNA-induced Silencing Complex (RISC). Typically the dsRNA precursor of nciRNA contains one or more nucleotide sequences that are complimentary to one or more non-coding RNAs that are to be targeted for down-regulation. The nciRNA precursor can be from 24 nucleotides to many kilo-bases in length. nciRNA precursors can be designed to encode nciRNAs that target one or more non-coding RNAs.

5. Activity of nciRNAs

In some embodiments the nciRNA is designed to induce sequence-specific degradation of the target non-coding RNA. In one embodiment the nciRNA provides an efficient mechanism of mortality in eukaryotic cells. The targeting of non-coding RNAs offers a variety of new targets with utility in basic research and in applications ranging from medicine to agriculture.

6. Modifications

In some embodiments RNA designed for nciRNA activity, or precursor polynucleotide is designed to include a nucleotide sequence that confers a function not directly associated with RNA interference. Exemplary functions include, but are not limited to purification, targeting or identification of the nciRNA or precursor. In some embodiments the RNA includes a sequence that assists in the purification of RNA. In one embodiment the sequence that assists in purification forms an RNA aptamer. In another embodiment the RNA is designed to contain a sequence that enables the targeting of the expressed RNA to a particular location within the cell or outside of the cell, or enables incorporation of the RNA into a cellular pathway or process. In one embodiment the targeting sequence enables incorporation of the RNA into a viral or bacteriophage capsid. A single RNA may contain one or more modification sequences that confer different properties or functions to the RNA. In some embodiments the RNA is designed to include a sequence to assist purification in addition to a sequence that confers high affinity for a bacteriophage or viral coat protein. In one embodiment a recognition tag is at the opposite end of the RNA polynucleotide to a purification tag.

In some embodiments genes are designed to include accessory elements to facilitate cloning into appropriate expression vectors for the expression the desired RNAs. The genes can be designed for the expression of single or double-stranded RNAs.

B. Compositions for Delivery, Storage and Protection

Compositions for the delivery, protection and storage of nciRNA and precursor polynucleotides are disclosed. Virus-like particles (VLPs) can protect enclosed RNAs from chemical, photo- and enzymatic degradation. The RNA in a VLP is stabilized against degradation by nucleases, hydroxyl radical, UV light, and $Mg^{2+}$-mediated inline attack. VLPs eliminate requirements for chemical modification to stabilize and deliver RNA. The high-stability of VLPs containing RNAs enables storage for long periods of time and allows for a broad range of application methods, including distribution as aerosols, solutions, powders, etc. The VLPs containing RNAs are readily taken up by many cell types and efficiently deliver RNA to biological targets. Furthermore, production and usage of VLPs containing RNA is water-based and environmentally sound.

1. Virus-Like Particles Containing nciRNAs

In some embodiments nciRNAs or precursor polynucleotides are enclosed within virus-like particles (VLPs) to facilitate production, storage, protection and delivery of the nciRNA or precursor polynucleotides. VLPs are symmetric, multi-protein structures that self-assemble into 30 nm-scale particles with virus-like morphology. On their exterior, VLPs resemble bacteriophages and viruses, but internally, VLPs can lack native genomic material (RNA or DNA required for integration, reverse transcription, replication, infection, etc.). Mutations and chemical modifications of VLP surfaces confer a variety of chemical and physical properties to VLPs. VLPs can be engineered as nano-containers that protect and deliver 'cargo' such as nciRNAs.

VLPs that contain RNA designed for interference activity of non-coding RNAs (nciRNAs) or precursor polynucleotides of nciRNAs are called "VLP-nciRNAs". VLPs containing nciRNAs offer several advantages over traditional RNA synthesis, packaging and delivery methods. VLPs containing nciRNAs are disclosed for the delivery of one or more nciRNAs or precursor polynucleotides within a viral capsid vessel. RNAs can be designed for production of VLPs containing nciRNAs in a single-step process, according to the disclosed compositions and methods. In one embodiment RNA is designed for use in a simple, robust, general and adaptable in vivo system (in *Escherichia coli*) that spontaneously produces and packages the RNA into VLPs. To enable packaging of RNA within VLPs, nciRNAs or precursor polynucleotides are designed to include a nucleotide sequence that is a viral coat protein recognition tag. In certain embodiments the nucleotide sequence that is a viral coat protein recognition tag is a hairpin structure which enables spontaneous uptake and assembly into VLPs. Recognition tags that confers high affinity for a bacteriophage or virus coat protein are known in the art and include, but are not limited to the enterobacteria q beta bacteriophage coat protein (See, for example, Witherell, et al., *Biochemistry*, 28:71-76 (1989)) and the PP7 coat protein (see Lim and Peabody, *Nucleic Acids Res.*, 30 (19) 4138-4144 (2002)). In one embodiment the recognition tag is a 29-nucleotide RNA hairpin structure specific for the bacteriophage q beta coat protein.

In one embodiment the sequence of the RNA tag is 5'

```
                                              (SEQ ID NO: 2)
CAGCAAGUUCCGCAACCGUA UCAAAACGUAAAUUACUCGGAC 3'.
```

The VLPs containing nciRNAs include bacteriophage or viral coat proteins. Coat proteins are known in the art and include the enterobacteria bacteriophage Q beta coat protein and the bacteriophage PP7 coat protein. An exemplary nucleotide sequence for genes encoding the bacteriophage Q beta coat protein gene is An exemplary amino acid sequence for the bacteriophage Q beta coat protein gene is

```
                                              (SEQ ID NO. 4)
           10         20         30         40
    MAKLETVTLG NIGKDGKQTL VLNPRGVNPT NGVASLSQAG 50         60         70         80
    AVPALEKRVT VSVSQPSRNR KNYKVQVKTQ NPTACTANGS 90        100        110        120
    CDPSVTRQAY ADVTFSFTQY STDEERAFVR TELAALLASP

130
    LLIDAIDQLN PAY.
```

III. Methods of Making and Using nciRNA

RNA designed for interference of non-coding RNA targets or nciRNA precursor polynucleotides can be produced in vivo using standard techniques. VLPs containing nciRNA and/or precursor polynucleotides can be produced in a single step process, according to the disclosed methods. nciRNA technology has a broad range of potential applications.

A. Production of nciRNAs

1. Expression of RNA nciRNAs or precursor polynucleotides can be expressed by any of the means for producing RNAs that are known in the art. Typically the gene or genes encoding RNA polynucleotide(s) are cloned into an expression system for expression of the RNA in vivo. In some embodiments, the in vivo expression of RNA occurs in a prokaryote. Useful prokaryotic and eukaryotic systems for expressing and producing polypeptides are well known in the art. An exemplary strain of *Escherichia coli* used to express the protein and RNA is the BL21(DE3) strain.

Expression cassettes that are designed for the transcription of nciRNA or precursor polynucleotides can be easily transferred to a transformation vector for transfer to the host organism. Representative transformation vectors and transformation techniques are well known in the art. In some embodiments the transcription system produces both strands and the RNA is dsRNA.

In one embodiment the coat protein is expressed in the pCDF-1b expression vector. Typical expression vectors for the expression of RNA include pET-28b and pUC-19.

In some embodiments the expression system is an inducible expression system. Inducible expression systems are known in the art (see, for example, Studier, *Protein Expr Purif,* 41: 207-234. (2005)). Prokaryotes commonly utilized for the expression of iRNA include, but are not limited to bacteria such as *Escherichia* spp., *Bacillus* spp. and *Thermophilus* spp.

```
(SEQ ID NO. 3) from GenBank: M99039.1.
 46   atggc aaaattagag 61   actgttactt taggtaacat cgggaaagat ggaaaacaaa ctctggtcct caatccgcgt 121   ggggtaaatc ccactaacgg cgttgcctcg ctttcacaag cgggtgcagt tcctgcgctg 181   gagaagcgtg ttaccgtttc ggtatctcag ccttctcgca atcgtaagaa ctacaaggtc 241   caggttaaga tccagaaccc gaccgcttgc actgcaaacg gttcttgtga cccatccgtt 301   actgccagg catatgctga cgtgaccttt tcgttcacgc agtatagtac cgatgaggaa 361   cgagcttttg ttcgtacaga gcttgctgct ctgctcgcta gtcctctgct gatcgatgct 421   attgatcagc tgaacccagc gtattga
```

The one or more genes encoding nciRNA or precursor polynucleotides and the one or more genes encoding the coat protein of a bacteriophage or virus can be encoded within the same expression construct, or may be encoded within two or more different expression constructs. The genes can be under the control of the same or different promoter elements. In some embodiments the expression of the VLP containing RNA is under the control of an inducible promoter. An exemplary inducible promoter is the Isopropyl-β-D-thiogalactopyranoside (IPTG) inducible promoter.

2. Production of VLPs Containing nciRNAs

The use of VLPs to enclose RNA further extends the range of potential nciRNA applications and facilitates the storage and delivery of nciRNAs. Methods for single-step production of VLPs containing nciRNAs are disclosed. The methods can be used, for example, for the production of nciRNA or precursor polynucleotides and packaging into VLPs. Typically, the expression of the RNA in a prokaryotic expression system is greater when the RNA is sequestered and packaged into VLPs than when RNA is produced alone. The nciRNA or precursor polynucleotides and VLPs self-assemble with high specificity into VLPs containing nciRNAs when the RNA is fused to an appropriate tag (for example, an RNA hairpin sequence). The methods do not impose any limitation on the structure of nciRNAs or precursor polynucleotides. VLP packaged RNAs can be long or short, single-stranded or double-stranded, and be a few nucleotides to many kilo-bases in length.

For the expression of VLPs containing nciRNAs or precursor polynucleotides a host organism is engineered to express genes for the coat protein of a bacteriophage or virus in addition to one or more nciRNAs or precursor polynucleotides that include a nucleotide sequence that is a viral coat protein recognition tag. The recognition tag enables the spontaneous uptake and assembly of the RNA into the VLP. Recognition tags that confer high affinity for bacteriophage or virus coat proteins are known in the art. Techniques and methods for the design and production of recombinant expression constructs to express RNAs are well known in the art. Techniques and methods for the design and production of recombinant expression constructs to express the coat proteins of a bacteriophage or virus are also well known in the art (see above). In some embodiments the genes encoding nciRNA are included within the same expression vector as the genes encoding the viral coat proteins. In some embodiments the genes encoding an nciRNA or precursor polynucleotides and the genes encoding the viral coat proteins are under the control of the same promoter. The promoter can be an inducible promoter. In some embodiments the host organism for in vivo production of VLPs containing nciRNAs is Escherichia coli.

The disclosed methods provide genes encoding the expression of one or more nciRNAs or precursor polynucleotides and genes encoding viral or bacteriophage coat proteins that spontaneously assemble in vivo into intact s VLPs that encapsulate the nciRNAs (VLP-nciRNAs). In one embodiment, nciRNAs or precursor polynucleotides are expressed in high yield in Escherichia coli.

In one embodiment the nciRNA or precursor polynucleotides within the VLP are at least 80% pure. In other embodiments the RNA is at least 85% pure, at least 90% pure, at least 95% pure or 100% pure. Typically one VLP vessel contains at least one nciRNA or precursor polynucleotide molecule. In some embodiments the molar ratio of RNA to VLP is 3.6. In other embodiments each VLP packs approximately three RNA polynucleotide molecules.

3. Purification

The purification of VLPs containing nciRNAs produced by the disclosed methods is trivial, and is simpler than the purification of unpackaged RNA.

Because of their distinctive size, properties and high stability, VLPs can be easily purified from Escherichia coli cellular lysates. Hence, the purification of VLPs containing nciRNAs produced by the disclosed methods is trivial, and is simpler than the purification of unpackaged RNA. Exemplary methods for the purification of VLPs include fast-protein liquid chromatography (FPLC), filtration, sedimentation, sucrose-gradient separation, and affinity tag chromatography. In some embodiments purification of the VLPs includes pelleting of the host organism cells. The pelleted cells or isolated VLPs containing nciRNAs can be frozen or dried for storage or distribution purposes.

4. Delivery

VLPs protect the enclosed nciRNAs or precursor polynucleotides from chemical, photo- and enzymatic degradation. The RNA in a VLP is stabilized against degradation by nucleases, hydroxyl radical, UV light, and $Mg^{2+}$-mediated inline attack. VLPs eliminate requirements for chemical modification to stabilize and deliver RNA. The high-stability of VLPs containing nciRNAs enables storage for long periods of time and allows for a broad range of application methods, including distribution as aerosols, solutions, powders, etc. The VLPs are readily taken up by many cell types and efficiently deliver nciRNA to biological targets. Furthermore, production and usage of VLPs containing nciRNA is water-based and environmentally sound.

In one embodiment VLPs containing nciRNAs are introduced into a complex eukaryotic organism by ingestion of doped food. When the VLP-nciRNAs are taken up by target cells, the RNA is released and the biological activity of the RNA is manifest. VLPs containing nciRNAs can be delivered as crude cell extracts. In other embodiments they can be left within the pelleted Escherichia coli and delivered as intact Escherichia coli cells.

B. Methods of Using nciRNAs

1. Agriculture

In some embodiments nciRNAs are used for the protection of plants from weeds and insects and for increasing crop yields. In certain embodiments, the targeting of gene expression by nciRNAs enables the production of allergy-free peanuts and decaffeinated coffee beans. In one embodiment, VLP-nciRNAs are used to produce and deliver RNA to kill mites that parasitize honeybees.

2. Therapeutics nciRNA technology has broad application in Therapeutics. In some embodiments VLP-RNAs are used for the delivery of nciRNA for applications in therapeutics. In certain embodiments, the targeting of gene expression by nciRNAs is an effective therapeutic strategy against infectious disease. In one embodiment, nciRNAs are used as a RNA-based functional cure for infection with protozoans. Exemplary protozoan parasites include Giardia lamblia, Entamoeba histolytica and Toxoplasma gondii.

EXAMPLES

Example 1

Construction of a VLP-RNA

Materials and Methods

RNA Design and Expression

Using known methods, one or more genes are built by recursive PCR or are cloned from a cDNA or genomic library. The genes, along with promoters and terminators, are DNA sequences designed to express the desired RNAs.

The genes can be of any desired sequence and can encode either double-stranded or single-stranded RNAs. RNAs of essentially any length and sequence can be produced in high yield in *Escherichia coli*. The RNA gene(s) are cloned into an inducible expression system.

Assembly and Purification of VLPs Containing RNA.

The RNA is designed to contain a recognition tag that confers high affinity for a bacteriophage or virus coat protein along with a known aptamer for RNA purification, if necessary. The recognition tag facilitates efficient packaging of the RNA into the VLP.

In this process, *Escherichia coli* are transformed with plasmids that express the RNA gene(s) in addition to genes for the coat protein of a bacteriophage or virus. The expressed coat protein spontaneously assembles in vivo into intact VLP-RNAs (VLPs that encapsulate RNAs). Because of their distinctive size, properties and high stability, VLPs can be easily purified from *Escherichia coli* cellular lysates.

Delivery.

Purified VLP-RNAs can be introduced into a complex eukaryotic organism by ingestion of doped food. When the VLP-RNAs are taken up by target cells, the RNA is released and the biological activity of the RNA is manifest. VLP-RNAs can be delivered as crude cell extracts. In addition they can be left within the pelleted *Escherichia coli* and delivered as intact *Escherichia coli* cells.

Results

A simple, robust, general and adaptable in vivo system in *Escherichia coli* that produces and packages RNA into VLPs was built. An integrated process for (i) Simultaneous overproduction of RNA and a bacteriophage coat protein, (ii) in vivo self-assembly of VLP-RNAs, was designed, constructed and successfully tested.

RNA was packaged into a VLP by co-expression of the capsid protein and the iRNA in vivo. The RNA, which was obtained by disruption of purified VLPs, contains a capsid binding tag along with a secondary affinity tag at a termini for optional purification. The RNA, including the duo tags, is 751 nucleotides in length, corresponding to the brightest band in the lane on the LH side. Integration of the band intensities on the gel indicates that the RNA is 80% pure. Comparison of quantity of VLP capsid protein with encapsulated RNA indicates an RNA/VLP molar ratio of 3.6. This ratio indicates that, on average, one VLP packs about three RNA molecules (see FIG. 1).

These data demonstrate that VLP-RNAs assemble and are efficiently packaged with the tagged-RNA when both coat protein and RNA are over produced in *Escherichia coli*. VLP-RNAs, the protein and RNA components of VLP-RNAs were purified and characterized (see FIG. 1).

Example 2 nciRNAs Selectively Target and Kill Target Insects

Materials and Methods nciRNA Design and Expression.

Using known methods, one or more genes are built by recursive PCR or are cloned from a cDNA or genomic library. The genes, along with promoters and terminators, are DNA sequences designed to express the desired nciRNAs. The genes can be of any desired sequence and can encode either double-stranded or single-stranded nciRNAs. nciRNAs of essentially any length and sequence can be produced in high yield in *Escherichia coli*. The nciRNA gene(s) are cloned into an inducible expression system.

Strategy nciRNAs can be easily purified from *Escherichia coli* cellular lysates. Furthermore, purified nciRNAs can be introduced into a complex eukaryotic organism by ingestion of doped food. When the nciRNAs are taken up by target cells, the biological activity of the nciRNA is manifest. nciRNAs can be delivered as crude cell extracts. In addition they can be left within the pelleted *Escherichia coli* and delivered as intact *Escherichia coli* cells.

Selection of Genes

*Reticulitermes flavipes* was chosen as a suitable model system to test the activity of nciRNA to selectively targets and kill an insect. Accordingly, nciRNA$^{aPTC}$ was designed to act by degrading the core of the large subunit ribosomal RNA (28S rRNA). The nciRNA sequence was based on the most highly conserved 23S/28S rRNA sequences, as described in Hsiao, et al.

The sequence of the RNA used includes 5'

```
                                                    (SEQ ID NO: 1)
rGUCCGAGUAAUUUACGUUUUGAUACGGUUGCGGAACUUGCGGGGUGCC

UAUUGAAGCAUGAGCCGGCGACUCAGCCGUAAGGCUGGACCCGAAACC

GGGCGAGCUAGCCCUGGCCAGCCGUAAGGCGAACCGGUGGGGGAUGCA

AACCCCUCGGAUGAGCUGGGGCUAGGAGUGAAAAGCUAACCGAGCCCG

GAGAUAGCUGGUUCUGCCGUAAGGCAGCGUUGCCGUAAGGCAAGUGCG

AAUGCCGGCAUGAGUAACGAGCGGGAGAACCCUCGCCAAGGAACUCUG

CAAGCCGUAAGGCCUCUGGCGACUGUUUACCAAAAACACAGCGCCGUAA

GGCGCGAGCCGUAAGGCUAACGACCGGAGCGCUGUCUCGGCGAGGGACC

CGGUGAAAUUGAACUGGCCGUGAAGAUGCGGCCUACCCGUGGCAGGAC

GAAAAGACCCCGUGGAGCUUUACUGCCGUAAGGCAGUUUGACUGGGGC

GGUCGGCCGUAAGGCUAAAAGUUACCCCGGGGAUAACAGGCUGAUCGC

CGUAAGGCGGUUUGGCACCUCGAUGUCGGCUCGUCGCGCCGUAAGGCU

UGGGCUGUUCGCCCAUUAAAGCGGCACGCGAGCUGGGUUCAGAACGUC

GUGAGACAGUUCGGUCUCUAUCCGCCACGGGCUUCCUCGUGCUUAGUA

ACUAAGGAUGAAAUGCAUGUCUAAGACAGCAUCUUCGC 3'.
```

Delivery and Assay for Efficacy of nciRNAs

A test for delivery of a nciRNA to a biological was carried out in *Reticulitermes flavipes*. 505 nucleotides of rRNA containing highly conserved rRNA sequences, linked together to form a single RNA molecule, were readily expressed as nciRNA$^{aPTC}$. A solution containing 300 μg of nciRNA$^{aPTC}$ was added each day to filter paper and the survival of *Reticulitermes flavipes* workers consuming the nciRNA$^{aPTC}$ doped paper was monitored throughout 14 days. A control group of termites consumed filter paper treated with buffer alone.

Results

Figure 3:
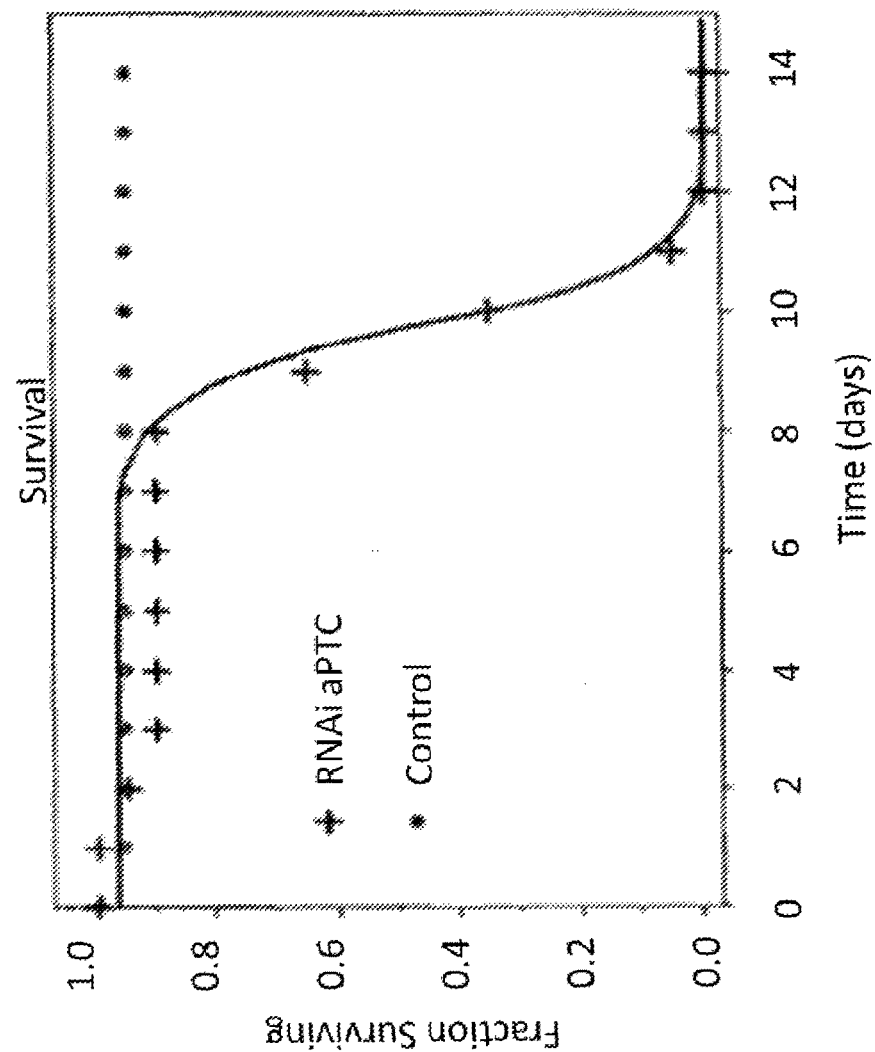
FIG. 3 is a scatter dot plot of synthesized data intended to illustrate the survival of the Eastern subterranean termite *Reticulitermes flavipes* (as a fraction of the starting quantity), over time (in days), for termites consuming filter paper containing 300 μg nciRNA$^{aPTC}$(+) or a control containing buffer (●), respectively.
Figure 4:
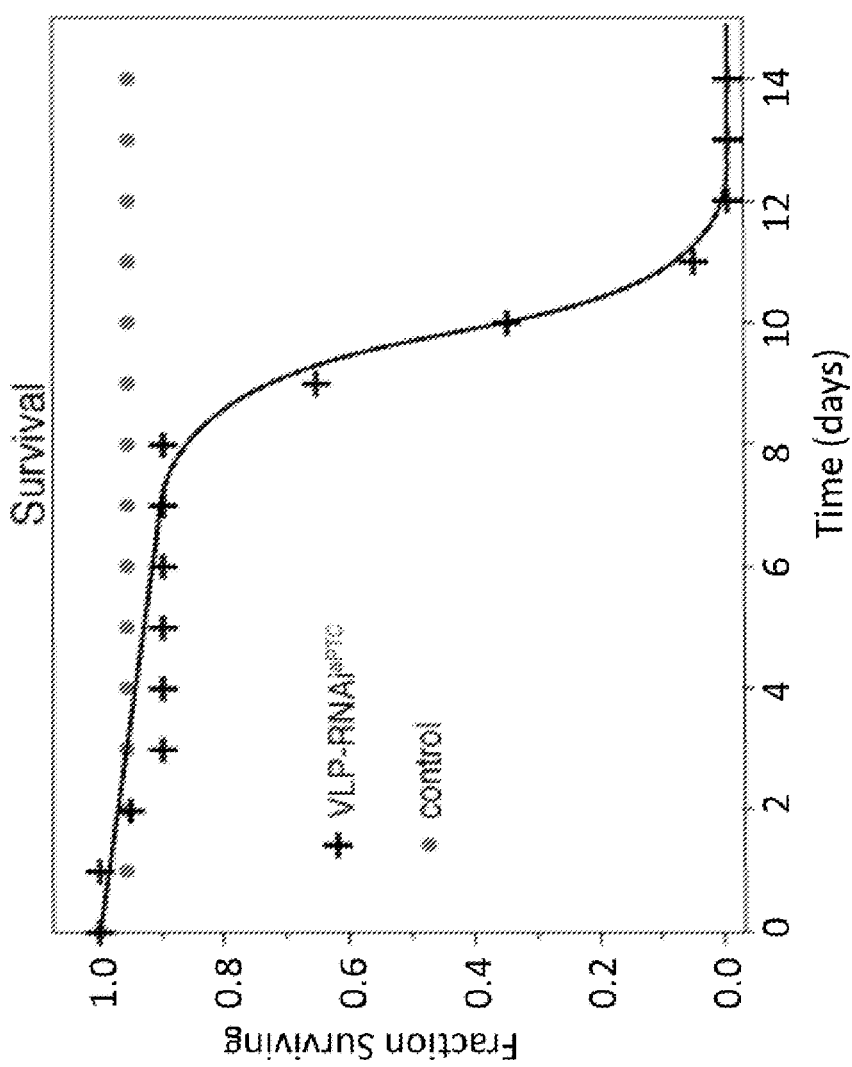
FIG. 4 is a scatter dot plot to illustrate the survival of the Eastern subterranean termite *Reticulitermes flavipes* (as a fraction of the starting quantity), over time (in days), for termites consuming filter paper containing 600 μg VLP-nciRNA$^{aPTC}$(+) or a control containing buffer (●), respectively.

Efficacy of nciRNAs nciRNA$^{aPTC}$ was successfully introduced into food and taken up by the insect *Reticulitermes flavipes*. When nciRNA$^{aPTC}$ was delivered to the insect via doped food, it degraded the insect 28S rRNA and killed *Reticulitermes flavipes* with great efficiency, leading to complete mortality by day 12 (FIG. 3). Control termites, which consumed filter paper treated with buffer alone, survived indefinitely.

Example 3 nciRNAs within VLPs (VLP-nciRNAs) Selectively Target and Kill Target Insects Materials and Methods Assembly of VLPs Containing nciRNA The nciRNA is designed to contain a recognition tag that confers high affinity for a bacteriophage or virus coat protein along with a known aptamer for RNA purification, if necessary. The recognition tag facilitates efficient packaging of the nciRNA into the VLP. In this process, *Escherichia coli* are transformed with plasmids that express the nciRNA gene(s) in addition to genes for the coat protein of a bacteriophage or virus. The expressed coat protein spontaneously assembles in vivo into intact VLP-nciRNAs (VLPs that encapsulate nciRNAs).

Strategy

Because of their distinctive size, properties and high stability, VLPs can be easily purified from *Escherichia coli* cellular lysates. Furthermore, purified VLP-nciRNAs can be introduced into a complex eukaryotic organism by ingestion of doped food. When the VLP-nciRNAs are taken up by target cells, the nciRNA is released and the biological activity of the nciRNA is manifest. VLP-nciRNAs can be delivered as crude cell extracts. In addition they can be left within the pelleted *Escherichia coli* and delivered as intact *Escherichia coli* cells.

Selection of Genes

*Reticulitermes flavipes* was chosen as a suitable model system to test the activity of VLP-nciRNA to selectively target and kill an insect. Accordingly, VLP-nciRNA$^{aPTC}$ was designed to act by degrading the core of the large subunit ribosomal RNA (28S rRNA). The nciRNA sequence was based on the most highly conserved 23S/28S rRNA sequences, as described in Hsiao et al.

Delivery and Assay for Efficacy of VLPs Containing nciRNAs

A test for delivery of nciRNA to a biological target using VLP-nciRNAs was subsequently carried out in *Reticulitermes flavipes*. 505 nucleotides of rRNA containing highly conserved rRNA sequences, linked together to form a single RNA molecule, were readily packaged into a VLP to give VLP-nciRNA$^{aPTC}$. A solution containing 600 μg of VLP-nciRNA$^{aPTC}$ was added each day to filter paper and the survival of *Reticulitermes flavipes* workers consuming the VLP-nciRNA$^{aPTC}$ doped paper was monitored throughout 14 days. A control group of termites consumed filter paper treated with buffer alone.

Results

Assembly of VLPs Containing nciRNA nciRNAs and a bacteriophage coat protein were simultaneously overproduced using the expression system in *Escherichia coli*. VLP-nciRNAs were purified from *Escherichia coli* lysates and the protein and nciRNA components were characterized. The nciRNA was 90% pure within the VLP.

Efficacy of VLPs Containing nciRNA

VLP-nciRNA$^{aPTC}$ was successfully introduced into food and taken up by the insect *Reticulitermes flavipes*. When VLP-nciRNA$^{aPTC}$ was delivered to the insect via doped food, it degraded the insect 28S rRNA and killed *Reticulitermes flavipes* with great efficiency, leading to complete mortality by day 12 (FIG. 4). Control termites, which consumed filter paper treated with buffer alone, survived indefinitely. The efficacy of the VLP-nciRNA$^{aPTC}$ in killing

*Reticulitermes flavipes* was equivalent to that of the nciRNA$^{aPTC}$ administered alone (FIG. 3).

REFERENCES

1. Zeltins A (2013) Construction and characterization of virus-like particles: A review. Mol Biotechnol 53: 92-107.
2. Smith M T, Hawes A K, Bundy B C (2013) Reengineering viruses and virus-like particles through chemical functionalization strategies. Curr Opin Biotechnol.
3. Rhee J K, Hovlid M, Fiedler J D, Brown S D, Manzenrieder F, Kitagishi H, Nycholat C, Paulson J C, Finn M G (2011) Colorful virus-like particles: Fluorescent protein packaging by the q beta capsid. Biomacromolecules 12: 3977-3981.
4. Pan Y, Zhang Y, Jia T, Zhang K, Li J, Wang L (2012) Development of a microrna delivery system based on bacteriophage ms2 virus-like particles. FEBS J 279:1198-1208.
5. Lau J L, Baksh M M, Fiedler J D, Brown S D, Kussrow A, Bornhop D J, Ordoukhanian P, Finn M G (2011) Evolution and protein packaging of smallmolecule RNA aptamers. ACS Nano 5: 7722-7729.
6. Zhou X, Wheeler M M, Oi F M, Scharf M E (2008) RNA interference in the termite *reticulitermes flavipes* through ingestion of double-stranded RNA. Insect Biochem Mol Biol 38: 805-815.
7. Bowman J C, Azizi B, Lenz T K, Roy P, Williams L D (2012) Preparation of long templates for RNA in vitro transcription by recursive PCR. In: Conn G L, editor. Recombinant and in vitro RNA synthesis: Methods and protocols, methods in molecular biology: Springer Science, LLC. pp. 19-41.
8. Studier F W (2005) Protein production by auto-induction in high density shaking cultures. Protein Expr Purif 41: 207-234.
9. Witherell G W, Uhlenbeck O C (1989) Specific RNA binding by q beta coat protein. Biochemistry 28: 71-76.
11. Milhavet O, Gary D S, Mattson M P (2003) RNA interference in biology and medicine. Pharmacol Rev 55: 629-648.
12. Whitehead K A, Langer R, Anderson D G (2009) Knocking down barriers: Advances in sirna delivery. Nat Rev Drug Discov 8: 129-138.
13. Oey M, Ross I L, Stephens E, Steinbeck J, Wolf J, Radzun K A, Kugler J, Ringsmuth A K, Kruse O, Hankamer B (2013) Rnai knock-down of Ihcbm1, 2 and 3 increases photosynthetic h2 production efficiency of the green alga *chlamydomonas reinhardtii*. PLoS One 8: e61375.
14. Huvenne H, Smagghe G (2010) Mechanisms of dsrna uptake in insects and potential of rnai for pest control: A review. J Insect Physiol 56: 227-235.
15. Lant B, Deny W B (2013) Methods for detection and analysis of apoptosis signaling in the *C. elegans* germline. Methods (San Diego, Calif.) 61: 174-182.
16. Haussecker D Http://maitherapeutics.Blogspot.Com/.
17. Haussecker D (2012) The business of mai therapeutics in 2012. Mol Ther Nucleic Acids 1: e8.
18. Wilson D N (2009) The A-Z of bacterial translation inhibitors. Crit Rev Biochem Mol Bio144: 393-433.
19. Ben-Shem A, Jenner L, Yusupova G, Yusupov M (2010) Crystal structure of the eukaryotic ribosome. Science 330: 1203-1209.

20. Anger A M, Armache J P, Beminghausen O, Habeck M, Subklewe M, Wilson D N, Beckmann R (2013) Structures of the human and *drosophila* 80s ribosome. Nature 497: 80-85.
21. Aurrecoechea C, Brestelli J, Brunk B P, Fischer S, Gajria B, Gao X, Gingle A, Grant G, Harb O S, Heiges M, Innamorato F, et al. (2009) Eupathdb: A portal to eukaryotic pathogen databases. Nucleic Acids Res.
22. Nicolas F E, Tones-Martinez S, Ruiz-Vazquez R M (2013) Loss and retention of RNA interference in fungi and parasites. PLoS Path 9.
23. Hsiao C, Lenz T K, Peters J K, Fang P Y, Schneider D M, Anderson E J, Preeprem T, Bowman J C, O'Neill E B, Lie L, Athavale S S, et al. (2013) Molecular paleontology: A biochemical model of the ancestral ribosome. Nucleic Acids Res 41: 3373-33.

We claim:

1. A noncoding inhibitory ribonucleicacid polynucleotide (nciRNA) comprising a nucleotide sequence complementary to a eukaryote non-coding RNA target (ncRNA)
   a) wherein binding of the nciRNA to the target ncRNA causes degradation of the target ncRNA;
   b) wherein the target ncRNA is ribosomal RNA (rRNA); wherein the nciRNA is produced within the eukaryote by processing of a single-stranded RNA precursor comprising the sequence of SEQ ID NO: 1.

2. The nciRNA of claim 1, wherein the single-stranded RNA precursor further comprises a polynucleotide sequence for purification of the RNA.

3. The nciRNA of claim 1, wherein the single-stranded RNA precursor further comprises a nucleotide sequence that has high affinity for a bacteriophage or viral capsid protein and enables incorporation of the single-stranded RNA precursor polynucleotide to within a viral particle.

4. The nciRNA of claim 1, wherein the eukaryote is *Reticulitermes flavipes*.

5. The nciRNA of claim 1, wherein the target nciRNA is expressed in an organism within a phylogenetic kingdom selected from the group consisting of Animalia, Plantae, and Protista.

* * * * *

SEQUENCE LISTING

```
<160> NUMBER OF SEQ ID NOS: 4

<210> SEQ ID NO 1
<211> LENGTH: 712
<212> TYPE: RNA
<213> ORGANISM: Artificial Sequence
<220> FEATURE:
<223> OTHER INFORMATION: non-coding interfering RNA

<400> SEQUENCE: 1
guccgaguaa uuuacguuuu gauacgguug cggaacuugc ggggugccua uugaagcaug        60
agccggcgac ucagccguaa ggcuggaccc gaaaccgggc gagcuagccc uggccagccg       120
uaaggcgaac cgguggggga ugcaaacccc ucggaugagc uggggcuagg agugaaaagc       180
uaaccgagcc cggagauagc ugguucugcc guaaggcagc guugccguaa ggcaagugcg       240
aaugccggca ugaguaacga gcgggagaac ccucgccaag gaacucugca agccguaagg       300
ccucuggcga cuguuacca aaaacacagc gccguaaggc gcgagccgua aggcuaacga        360
ccggagcgcu gucucggcga gggacccggu gaaauugaac uggccgugaa gaugcggccu       420
acccguggca ggacgaaaag accccguga gcuuuacugc cguaaggcag uuugacuggg        480
gcggucggcc guaaggcuaa aaguuacccc ggggauaaca ggcugaucgc cguaaggcgg       540
uuuggcaccu cgaugucggc ucgucgcgcc guaaggcuug ggcuguucgc ccauuaaagc       600
ggcacgcgag cugggucag aacgucguga gacaguucgg ucucuauccg ccacgggcuu        660
ccucgugcuu aguaacuaag gaugaaaugc augucuaaga cagcaucuuc gc              712

<210> SEQ ID NO 2
<211> LENGTH: 42
<212> TYPE: RNA
<213> ORGANISM: Artificial Sequence
<220> FEATURE:
<223> OTHER INFORMATION: RNA tag

<400> SEQUENCE: 2
cagcaaguuc cgcaaccgua ucaaaacgua aauuacucgg ac                          42

<210> SEQ ID NO 3
<211> LENGTH: 402
<212> TYPE: DNA
<213> ORGANISM: Bacteriophage Q beta

<400> SEQUENCE: 3
atggcaaaat tagagactgt tactttaggt aacatcggga aagatggaaa acaaactctg        60
gtcctcaatc cgcgtggggt aaatcccact aacggcgttg cctcgctttc acaagcgggt       120
gcagttcctg cgctggagaa gcgtgttacc gtttcggtat ctcagccttc tcgcaatcgt       180
aagaactaca aggtccaggt taagatccag aacccgaccg cttgcactgc aaacggttct       240
tgtgacccat ccgttactcg ccaggcatat gctgacgtga ccttttcgtt cacgcagtat       300
```

```
agtaccgatg aggaacgagc ttttgttcgt acagagcttg ctgctctgct cgctagtcct    360
ctgctgatcg atgctattga tcagctgaac ccagcgtatt ga                        402

<210> SEQ ID NO 4
<211> LENGTH: 133
<212> TYPE: PRT
<213> ORGANISM: Bacteriophage Q beta

<400> SEQUENCE: 4

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
        50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
            115                 120                 125

Leu Asn Pro Ala Tyr
        130
```